(12) United States Patent
Dalton

(10) Patent No.: US 8,313,441 B2
(45) Date of Patent: Nov. 20, 2012

(54) NEUROAUDIOLOGICAL CENTRAL AUDITORY TEST APPARATUS AND METHOD OF DIFFERENTIATION OF THE NEURAL CORRELATES IN PTSD, TBI, AUTISM, ADHD, ET AL

(75) Inventor: Leslie Dalton, Canyon, TX (US)

(73) Assignee: Dichonics Corporation, Amarillo, TX (US)

( * ) Notice: Subject to any disclaimer, the term of this patent is extended or adjusted under 35 U.S.C. 154(b) by 95 days.

(21) Appl. No.: 13/046,277

(22) Filed: Mar. 11, 2011

(65) Prior Publication Data

US 2011/0295166 A1    Dec. 1, 2011

Related U.S. Application Data

(60) Provisional application No. 61/339,951, filed on Mar. 11, 2010.

(51) Int. Cl.
*A61B 5/00* (2006.01)

(52) U.S. Cl. ........................................ 600/559

(58) Field of Classification Search ................ 73/585; 600/25, 559; 381/71.1, 71.6, 73.1, 312, 317
See application file for complete search history.

(56) References Cited

U.S. PATENT DOCUMENTS 4,556,069 A * 12/1985 Dalton et al. ................ 600/559
4,759,070 A *  7/1988 Voroba et al. ................ 381/60

* cited by examiner

*Primary Examiner* — Max Hindenburg
*Assistant Examiner* — Jonathan M Foreman
(74) *Attorney, Agent, or Firm* — J. Wiley Horton

(57) ABSTRACT

An apparatus, software, procedures and technology that, beginning with a simple manipulative auditory paradigm, moves up the auditory neural pathways, modifying the basic stimulus from a unilateral routine audiology tool to a dichotic central auditory processing diagnostic tool that defines hearing loss along the entire auditory chain from the middle ear to the cortex. From the resultant data comes information related to the reduction of tinnitus employing parathreshold central procedures rather than the traditional suprathreshold masking or phase-shifting techniques. The new application modifies and applies known technology in new ways for both the top-down and bottom-up differential diagnosis of auditory disorders and the tinnitus reduction.

1 Claim, 17 Drawing Sheets

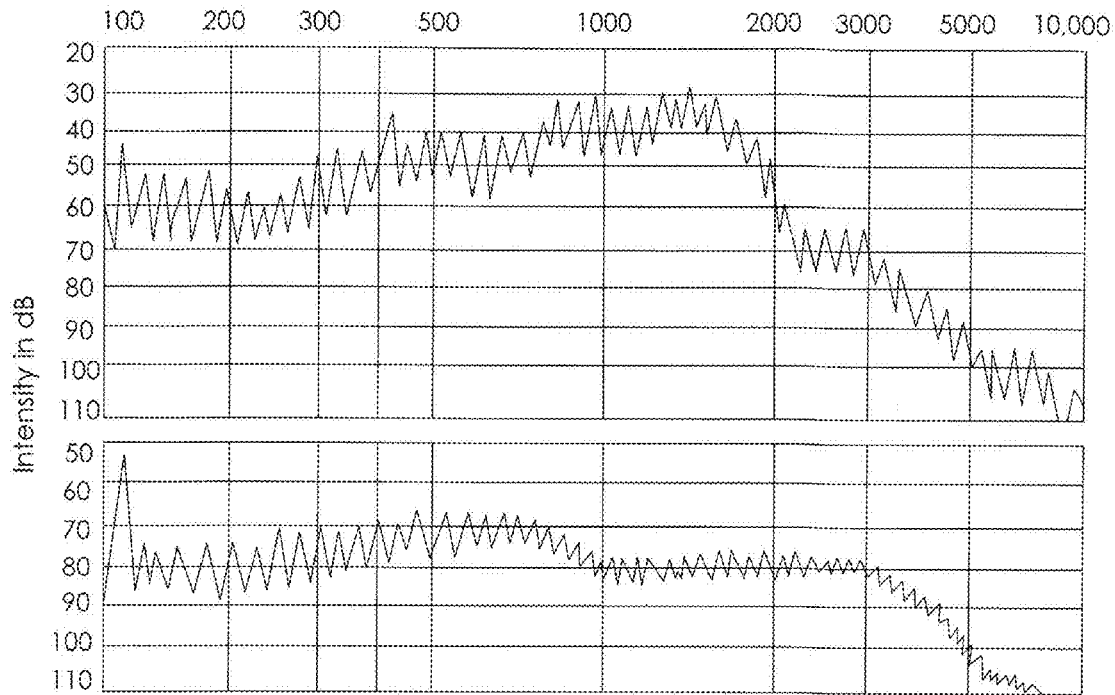

Fig 4-57. Pathological types of audiograms. The upper curve was obtained from an ear with conductive deafness, the lower one from an ear with perceptive deafness

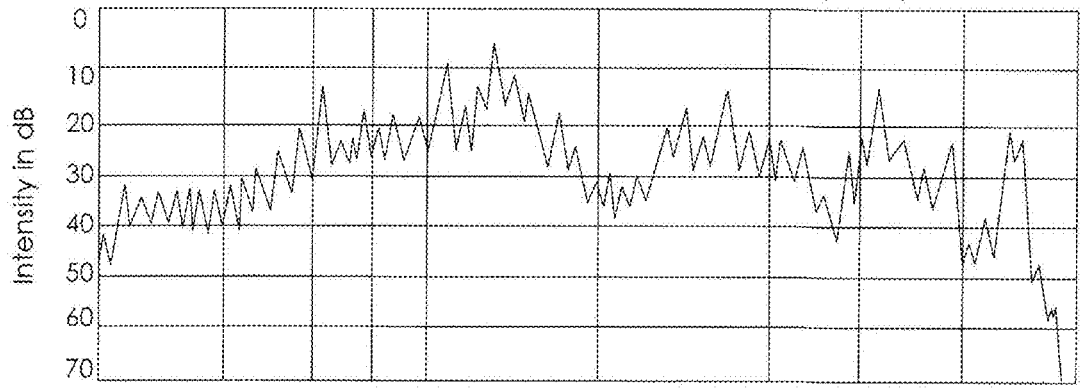

Fig 4-58. An audiogram from an ear suffering tinnitus.

Fig 7. Note: (George Von Bekesy, Experiment in Hearing, McGraw Hill, 1960). Bekesey used a single continuous tracing to plot a conductive hearing loss (top), a sensorineural hearing loss (middle) and one with tinnitus (bottom)

FIG. 7

NEUROAUDIOLOGICAL CENTRAL AUDITORY TEST APPARATUS AND METHOD OF DIFFERENTIATION OF THE NEURAL CORRELATES IN PTSD, TBI, AUTISM, ADHD, ET AL

CROSS-REFERENCES TO RELATED APPLICATIONS

This application claims the benefit of an earlier-filed provisional patent application under 37 C.F.R. §1.53. The provisional application was assigned Ser. No. 61/339,951, with a filing date of Mar. 11, 2010. The provisional application listed the same inventor.

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of neuroaudiological differential diagnosis of the auditory system using a correlation of a unique "bottom-up" and "top-down" evaluation paradigm. The process uses both psychophysical and electrophysiological data collection techniques to measure the effects evoked by a single manipulated stimulus on the entire auditory system from the cochlea to the cortex.

2. Description of the Related Art

Tinnitus is defined as a persistent ringing, buzzing, or similar noise distraction in a patient's sensory perception of sound. The patient "hears" the phenomenon in the absence of an actual sound stimulus. Efforts to qualify and quantify tinnitus for the purpose of obliterating its debilitating effects have been protracted and expansive. The driving force in dealing with tinnitus has been the audiological measurement of suspected related hearing loss and the manipulation of maskers or phase-dependant stimuli to attempt to cover or cancel the offending noise(s). Since most tinnitus is tonal (a constant ringing), the logic has been that if the frequency of the tone could be isolated then a specific masking complex could be developed to cover up the offending tone.

Early conventional wisdom suggested that tinnitus was largely of cochlear origin but several studies have been recently conducted that point to the central nervous system as the origin. Recent studies have employed positron-emission tomography ("PET") to actually monitor cerebral blood flow ("CBF") in the central auditory system to see if tinnitus possibly resulted from excessive spontaneous activity in the central auditory system. These studies reported CBF changes in the left temporal lobe for patients with right ear tinnitus, whereas bilateral temporal lobe activity occurred in response to a peripheral tonal stimulation in the right ear.

The same studies concluded that tinnitus is not of cochlear origin but rather originates within the central auditory system since tones evoked more CBF activity in tinnitus sufferers than in control subjects.

Other studies have suggested that tinnitus has many similarities with the symptoms of neurological disorders such as paresthesia and central neuropathic pain caused by functional changes in specific parts of the central nervous system. Since much more is known about pain than tinnitus, the same studies suggested that it is possible to use pain as an algorithm to the understanding of the pathophysiology of tinnitus.

Subjective tinnitus can accompany hearing loss associated with exposure to loud sounds or noise trauma, after administration of ototoxic drugs, as a co-occurrence with presbycusis, as a part of the Ménière's syndrome, and as part of vestibular Schwannoma (as well as many other conditions). It also occurs as part of total deafness. Tinnitus is known to be comorbid with posttraumatic stress disorder, traumatic brain injury, and other psychological sequalae.

Tinnitus may appear as a nearly pure tone, distorted sound, hissings, or thumping; it can be manifested as recruitment of sound (an abnormal increase in perceived loudness as a sound is intensified), phonophobia (fear of sounds) or in cases where acoustic reflexes are changed. Tinnitus can be perceived as an external noise on one side, an external noise on both sides, or a noise within the head. There is evidence that the pathophysiology of unilateral and bilateral tinnitus is different. There is considerable evidence that expression of neural plasticity plays a central role in the development of the abnormalities that cause many forms of chronic subjective tinnitus.

Expression of neural plasticity can change the balance between excitation and inhibition in the nervous system, promote hyperactivity, and it can cause reorganization of specific parts of the nervous system or redirection of information to parts of the nervous system not normally involved in processing of sounds (non-classical or extralemniscal pathways). Since there are many kinds of subjective tinnitus, a search for a (single) cure for tinnitus is rather fruitless if not futile. Testing of new treatments is also hampered by the fact that it is not possible to distinguish between different forms of tinnitus for which different treatments may be effective.

Still other studies have linked tinnitus to central nervous system neurodegeneration. They used nuclear medicine brain imaging (i.e. PET) to study subjects with Alzheimer's disease and challenged the time-honored sensorineural view of subjective tinnitus and its subsequent clinical application for treatment. They concluded that subjective tinnitus occurs as the result of a central disorder.

Work has been done to explore the use of event related potentials (ERP) to study the pathogenesis of tinnitus and to attempt to correlate psychophysiological and neurophysiologic tinnitus and to better understand tinnitus decompensation. These studies used top-down event related potentials ("ERP") methodology. Other studies also used auditory evoked cortical potentials ("AECP") in the diagnosis of attention deficit disorder, etc and for studying tinnitus decompensation. A model of neural correlates to auditory attention reflected in AECPs using corticothalamic feedback dynamics was suggested. The model applies a multiscale of evoked potentials to the hearing path and discusses neuro functionality in terms of corticothalamic feedback loops related to focal and non-focal attention and objective tinnitus decompensation measure. Magnetic resonance spectroscopy ("MRS") to identify unique in vivo metabolic and neurobiochemical biomarkers associated with tinnitus in specific regions of the central nervous system ("CNS").

The emerging view is that treating the symptom is not effective and given the number of disorders comorbid with tinnitus a top-down analysis of the origin of tinnitus in conjunction with other neurological entities is needed. Patients who suffer from a variety of neurological disorders report tinnitus as an accompanying symptom. These disorders includes things such as central auditory processing disorders ("CAPD"), attention deficit hyperactivity disorder ("ADHD"), autism, dyslexia, learning disabilities, etc.

The proposed inventive method therefore focuses on the mapping of neurological disorders along the auditory pathways using dichotic stimuli in an array of psychophysical paradigm for tracking hearing defects along the total auditory pathway from the cochlea to the central auditory processing areas (bottom-up) verified by a top-down objective procedure using the very same stimuli.

Tinnitus results as a symptom of many primary auditory disorders rather than a unique pathology unto itself. In some cases treating the pathology will alleviate the tinnitus. In other cases the site of lesion of the primary disorder is unknown leaving the tinnitus as a phantom somewhere within the auditory network.

The present method uses a unique top-down neuroaudiological stimulus apparatus and procedures to place electric "markers" along the dichotic auditory pathways that can then be used in a bottom-up psychophysical paradigm to find those same "markers"—thereby assisting in the differential diagnosis of auditory problems from the cochlea to the cortex.

FIG. 1 is a conventional diagram of the main neural stations where "markers" can be placed using auditory evoked potentials ("AEP") techniques such as the well-established diagnostic procedure of auditory brainstem response ("ABR"). The use of a top-down CAPD event marker for a click stimulus in but one ear (monaural) is shown in FIG. 1.

The reader should note that ABR is an objective electrophysiological process that requires no psychophysical behavioral response from the patient. A monaural click stimulus delivered to either ear is shown as it passes bottom-up through the auditory pathways. The numbers shown on the waveform (a) reflect the marker point of emergence of neuroelectricity for each wave.

When binaural stimuli are presented, the interactive crossover at the marker points are neurologically modified to provide the brain with information far beyond monaural stimulation. One added set of information in the dichotic stimulus (stimulus to both ears) is the perceived location of the source of the sound. Each side of the brain processes information from the opposite side of the auditory system with the brainstem serving as the primary switchboard.

FIG. 1 represents the neural transmission of a monaural stimulus (a stimulus to only one ear). Note that a majority of the energy is sent to the opposite side of the brain from the stimulus. However, some neural tracts continue along the ipsilateral side of the neural pathways. When a binaural stimulus is simultaneously presented to both ears (diotic stimuli)—and each side of the auditory processing system is individually neurophysiologically recorded—the results appear as shown in FIG. 2.

FIG. 2 shows a plan view looking down on the top of a patient's head. Ground electrode 14 is placed on the midline. Left electrode 16 is placed proximate the patient's left ear. Right electrode 18 is placed proximate the patient's right ear. Left ear phone 20 delivers a stimulus to the left ear and right ear phone 22 delivers a stimulus to the right ear.

FIG. 2-a is a typical monaural waveform resulting from a stimulus applied to only one ear. FIG. 2-b shows data obtained from a three electrode montage (two measuring electrodes and one ground reference electrode) when a diotic stimulus (identical stimulus applied to each ear at exactly the same time) is applied.

A three electrode montage is rather simple and is presented only to convey the concept. The use of a more standard 20 electrode EEG montage will further identify unique dichotic cortical markers using brain electric activity mapping ("BEAM") with the same stimulus used in FIG. 2-b.

The reader will observe that the two waves shown in FIG. 2-b do not overlie each other. The brain map will reflect the lead/lag or lag/lead perceived position of the stimulus as a shift in the voltage of the electrodes along the cortex. This is sometimes referred to as a virtual image analysis ("VIA"). VIA refers to the brain's ability to analyze sound stimuli and create a virtual image of the location of the spatial location of the source of the sound. As will be explained in detail subsequently, a perfectly symmetric sound stimulus as shown in FIG. 2 is not perceived as a "centered" sound by the brain.

A "VIA setting" refers to the lead or lag of a stimulus applied to one ear versus the other. This lead or lag relationship alters the brain's perception as to the location of the source of the sound.

Brain electric activity mapping ("BEAM") maps the instantaneous electrical differential between a reference electrode (ground) and the balance of the electrode array mapped in different colors representing the relative voltages. FIG. 3 shows a typical brain map for two different VIA settings (one on FIG. 3-a and one in FIG. 3-b).

In keeping with the convention for patent drawings the images of FIG. 3 are not presented in color. However, it is important for the reader to understand that they are conventionally presented in color to a user of the inventive method.

FIG. 4 shows normal data for a right handed subject (FIG. 3-a shows the BEAM maps for the same stimulus). The reader will observe that right stimulus 26 is delivered through right earphone 22 slightly before left stimulus 24 is delivered through left ear phone 20. The auditory brainstem response waves 28 ("ABR waves") are closely matched from left to right (They lie closely over each other).

Changing the VIA setting (the lead-lag of the right versus left stimulus) will change the ABR wave configuration and the BEAM map. Changing the VIA lead-lag from left to right will "reverse" the ABR waves and the BEAM map depending on brain dominance (whether the patient is left brain dominant or right brain dominant). The VIA arrangement is reflected in an overall shift of the ABR assemblage with the dominant hemisphere waveforms appearing at an earlier time.

FIG. 5 shows the effect of changing the VIA setting on the resulting ABR waves. (See FIG. 5). Here the transformation that takes place as a result of lead/lag or lead/lag dichotic configuration is shown. As the VIA is increased the individual waveforms shift in time to a greater or lesser number. Likewise the right and left waveforms shift together but take on different "shapes" depending on the VIA differential. In addition the entire assemblage shifts in time linked to hemispheric dominance.

Psychophysical Auditory Phenomenon: (Normal Auditory Processing)

The brain is not unilaterally equal to auditory stimulation. This natural brain dominance accounts for sound localization (spatially locating the source of the sound) and is an important component in central auditory processing. Factored into this is the fact that the balance mechanism is part of the auditory system that may contribute to tinnitus. There is an optimum overlay pattern (of the left and right ABR waves) where the natural hemispheric dominance is tuned to the point where sound is localized to the center of the head (The patient perceives the sound as coming from the center of the head). The human ear can psychophysically detect a time change of as little as 64 usec using a 100 usec, 60 dB square wave as a dichotic stimulus. FIG. 4 shows the ABR correlate of the behavioral position of zero. As can be seen the actual dichotic neurological midline position is off center (meaning that the timing of the stimulus transmitted to the two ears must be varied in order to place the left and right ABR waves on top of each other).

FIG. 6 also shows this phenomenon. Purely diotic stimuli (in which a stimulus is presented simultaneously to each ear) produces a perception of the sound being off center to one side or the other (depending upon whether the individual is right brain dominant or left brain dominant).

Dichotic Listening

Historically Dichotic listening has been described as the simultaneous presentation of different stimuli to both ears. It appears that in dichotic stimulation, contralateral pathways from the ears to the opposite hemispheres suppress the ipsilateral pathways from the ears to the same hemispheres. In most right-handed persons there is a right ear advantage because the path from the right ear goes contralaterally to the dominant left hemisphere. In behavioral psychophysical procedures this process is reflected as a positional location about the head. If the time between two stimuli is varied in microseconds as lead/lag/or lag/lead the stimulus pair is reported to be moving from place to place about the head. Under earphones this positional location moves from being into both ears at larger time differentials and moves toward the center of the head as the time is lessened to ultimately focus at midline at approximately 100 microseconds lead/lag for normal right dominant subjects and vice versa for left dominant subjects. FIG. 5 shows this relationship for neurological studies and FIG. 6 show the psychophysical positioning (the term "psychophysical" meaning the user's perception of position). These responses are part of the bottom-up paradigm.

Bottom Up Diagnostic Processes

Tone decay, tinnitus and recruitment of loudness are three critical diagnostic indicators in the differential diagnosis of hearing disorders. Recruitment is a diagnostic indicator of cochlear pathology and is manifested as an abnormal growth of loudness. Tone decay occurs when a continuous tone appears to diminish as the tone is continued without change over a fixed period of time and is considered as an indicator of retrocochlear pathology. Tinnitus is discussed in detail later.

In the late 1940's, a "New Audiometer" was described that used the classical psychophysical method of adjustment to present constantly changing tones to a subject who alternately adjusted the intensity of those tones from the just noticeable difference (JND) to the just not noticeable difference (JNND) thereby crossing absolute threshold numerous times. This work resulted in the formulation of the classic Bekesy Audiograms that were later standardized into the four basic patterns. FIG. 7 shows Bekesy's own original classification (1960) of audiograms obtained on his New Audiometer. FIG. 7 shows a single continuous tracing to plot a conductive hearing loss (top), a sensorineural hearing loss (middle) and one with tinnitus (bottom).

Bekesy suggested that recruitment of loudness is demonstrated in the narrowing of the tracings following a pattern of normal excursions and retro-cochlear lesions are displayed as rapid tone decay. This work was extended by others to a continuous tone to an interrupted tone so as to reveal both tone decay and recruitment. Examples of Jerger's original classification of the Bekesy audiograms are shown in FIG. 8 (Type I, Normal; Type II, Cochlear; Type III and Type IV Retrocochlear).

The minimal auditory intensity differential ("MAID") used a single on-going stimulus to derive similar results as gained by the Bekesy audiograms. FIG. 9 shows the design of a MAID-type signal. If a constant intensity/frequency pure tone is varied in amplitude four times/sec with no rise-fall envelope (yet with no electrical switching transient), the change in intensity is perceived by a listener as (1) a difference limen ("difference limen" being synonymous with JND or "just noticeable difference") to intensity and (2) a four times per second click. The resultant perception is an ongoing two component stimulus which can be psychophysically manipulated to look at the relationship of a continuous to interrupted tone (see Bekesy Type III) while at the same time looking at the click perception threshold which yields recruitment data (see Bekesy Type II and IV). In retrocochlear lesions the click perception threshold is normal and the carrier puretone fades away leaving the patient only perceiving the four times per second click. Hence the MAID-type signal provides a psychophysical methodology for the determination of both cochlear and retrocochlear hearing disorders with a single stimulus. The perception of that change is dependant on the presence of the site of lesion and the degree of pathology. The MAID functions primarily as a cochlear/retrocochlear differential test.

The MAID-type signal can be made dichotic by presenting it to each ear independently. The right ear wave was kept constant and the left ear wave was "slid" (phase shifted) back and forth occurring either in a lead or a lag position. The perceived behavioral placement of the source of the sound on the head was dependant on the time of the lead/lag or lag/lead.

By changing the onset times of the signal to one ear with respect to the signal for the other ear a virtual image ("VIA") is established in the user's perception (the location of the sound source seems to change). If wave B is adjusted in time-steps from about 100 μsec to 2 msec the sound source appears to move from one ear, across the mid plane, and then to the opposite ear with the midpoint being perceived as being off-center.

Because of the complexity of the MAID stimulus a single click of 100 μsec duration (standard ABR stimulus) was delayed in the previously described lead/lag//lag/lead (VIA) version for electrophysiological application. (The new version of the stimulus presented in the inventive method returns to the roots of the MAID and changes the stimulus for electrophysiological use by removing only the puretone carrier).

FIG. 11 is a schematic of the VIA stimulus. The MAID envelope with only the removal of the puretone serves the same purpose as the VIA.

FIG. 12 is a diagram of the revised stimulus (The MAID envelope with only the removal of the puretone). This change generates a new stimulus only one component away from the MAID-type signal and becomes more reliable in the differential diagnosis paradigm. Furthermore the change in intensity ("ΔI") is situated onto a constant ongoing baseline stimulus rather than silence and allows for a more subtle change at the stimulus point.

Children: Neurological Disorders and Tinnitus

Any mention of central dysfunction should necessarily move into a discussion of central auditory processing disorders (CAPD) and, more specifically, labeled disorders such as autism and traumatic brain injury ("TBI") in children. Children are seldom included in the discussion of tinnitus even though they do suffer the disorder but, more importantly, they comprise the major population of sufferers of central neurological disorders. Tinnitus is present in child subjects with hearing loss and central sensory perception and emotional problems. When exploring the risk factors in children, a relationship was found between tinnitus and a history of noise exposure, motion sickness, hyperacusis and hearing loss. The coexistence of tinnitus and hyperacusis in these studies introduces the possibility that tinnitus might be a factor in disorders such autism and TBI.

Hyperacusis has been found in an autistic group when compared to controls. The use of biomarkers of brain injury has also been discussed in the field of TBI. TBI is a leading cause of emergency department care with seemingly minor head trauma account for approximately one-half of children with documented TBIs. Despite the frequency and importance of childhood minor head trauma, there exists no highly accurate, reliable and validated clinical scoring system or prediction rule for assessing risk of TBI among those with minor head trauma.

Hearing loss has four major diagnostic categories. The first two (peripheral) have clearly defined medical diagnostic indicators: (1) Conductive, due to obstruction or infection in the outer or middle ear and is identified via otoscopy, audiograms (air and bone conduction) and tympanometry; (2) sensorineural that occurs within the neural transduction system of the cochlea (including the semicircular canals) and is fairly accurately defined by way of audiograms, speech discrimination scores, recruitment, ENG and tone decay to a lesser degree (3) retrocochlear and brainstem that occurs within the VIIIth cranial nerve to the auditory cortex and is defined by tone decay testing, audiometry, ENG (etc), ABR and (4) Central occurring in the vestibulocerebellum that controls balance (input from the inner ears), eye movement and central auditory processing.

The third and fourth diagnostic categories comprise the central processing system which serves as an elaborate "switch board" that routes neural signals via the brainstem to ipsi/contralateral positions on the cortex and cerebellum. One common element of all of these hearing disorders is tinnitus. Given this coincidence of pathology and tinnitus, the presence of tinnitus in children with hearing disorders (conductive, cochlear, retrocochlear, or central) means that the probability of tinnitus being a disruptive development element is high.

Tinnitus and Auditory Processing

Measurement efforts in tinnitus have spanned the spectrum of diagnostic instruments and methods with psychoacoustics being the most favored technique even though some have suggested that the more commonly used behavioral information of pitch, loudness, maskability, and residual inhibition do not yield consistent relationship to the severity or perceived loudness of tinnitus. A search for psychophysical tools lead to the methods of bracketing, limits, and adjustment for the measurement of pitch in the ear ipsilateral to the tinnitus. Some have used strict psychoacoustics methodology to explore the reaction times of normal hearing subjects with and without tinnitus. Of importance to the present study is their finding that tinnitus sufferers had shorter reaction times at sensation levels near threshold than did normal patients— with no significant differences between groups at sound stimuli in the suprathreshold intensity range. Several studies have noted the tendency for near threshold activities to be more productive than louder ones.

Little quantitative measurement of tinnitus was possible before the development of the electric audiometer. Since then many attempts have been made to simulate the phenomenon. Frequency and masking measurements were first described in 1931 along with techniques involving loudness balance, free-field matching and taped sound effects. It has been suggested that a music synthesizer might be a more appropriate tool for tinnitus matching since the audiometer is limited in frequency selection.

One approach used a patient tracking psychophysical method using continuous sweeping frequencies (20 to 20 kHz) and determined this methodology to be much more productive than standard methods of audiometry.

Another study compared the hearing sensitivity and psychological profile of young subjects with tinnitus and normal hearing. The test procedures used pure-tones (including high frequencies), notched-noise, auditory-brainstem responses, and evoked otoacoustic emissions. Psychophysical and brainstem tests were comparable to those of normal hearing subjects without tinnitus. Otoacoustic emissions were "worse" in ears of tinnitus subjects and neurotic personality traits were stronger in the tinnitus subjects.

A psychometric numeric rating scale has been used to detail the different perceptual components of tinnitus; i.e. auditory sensations which are perceived in the absence of a corresponding external acoustic stimulus. Some such studies measured pitch (in 0.2% steps) and loudness (in 2 dB steps) of tinnitus using a forced-choice double-staircase procedure and found that the difference limen (JND) of pitch and loudness were not significantly different from that of the same measurements made to comparable external stimuli.

The most studied area of tinnitus has to do with masking the offending phenomenon. Early masking efforts employed psychoacoustics. More recent psychoacoustic studies have looked into central involvement as apposed to the severity of hearing loss. On masking technique used low-level ultrasound in an attempt to inhibit tinnitus. Another technique evaluated various electrical stimuli via the mastoid processes for their ability to suppress or relieve severe tinnitus.

Pulsed electromagnetic stimulation applied on the mastoid bone has offered little improvement. Experiments using lasers have also shown no significant results. Other experiments used two separate audio frequency generators to shift the phase of the second generator in relationship to the first generator (set at the audiometrically-determined frequency-matched monofrequency of the tinnitus) by 180 degrees so that a third sound was delivered simultaneously to both ears. This theory supposed that cancellation would result but in reality a third multi-frequency masking stimulus was produced that would randomly match the monofrequency tinnitus.

The past 15 years have seen the most change in tinnitus evaluation and management. The very active classical psychophysics research in audition of the 1930's set the stage for the use and understanding of psychoacoustics techniques. Studies of tinnitus masking and residual inhibition exploded in the 1970's, leading to the therapeutic use of masking and an increase in research of psychoacoustic measurement with pitch, loudness, maskability, and residual inhibition emerging as foci.

The ideal solution would be to cancel out tinnitus without introducing external noise. The next best solution would be to reduce or cancel the tinnitus as well as the intensity of the masking stimulus. The present invention presents a psychoacoustics technique that either totally cancels tinnitus or replaces it with a barely discernable external noise of lesser volume and no pitch characteristics. The approach takes advantage of several well known, and some lesser known, auditory neurological patterns of change that occur in both normal and pathological ears including, but not limited to (1) binaural summation; (2) temporal asymmetry; (3) "recruitment" and tone decay; and (4) dichotic brain dominance.

BRIEF SUMMARY OF THE INVENTION

This patent application describes apparatus, software, procedures and technology that, beginning with a simple manipulative auditory paradigm, moves up the auditory neural pathways, modifying the basic stimulus from a unilateral routine audiology tool to a dichotic central auditory processing diagnostic tool that defines hearing loss along the entire auditory chain from the middle ear to the cortex. From the resultant data comes information related to the reduction of tinnitus employing parathreshod central procedures rather than the traditional suprathreshold masking or phase-shifting techniques. The new application modifies and applies known technology in new ways for both the top-down and bottom-up differential diagnosis of auditory disorders and the tinnitus reduction.

BRIEF DESCRIPTION OF THE SEVERAL VIEWS OF THE DRAWINGS

FIG. 7 is a schematic view, showing data from individuals suffering from hearing loss.

Figure 1:
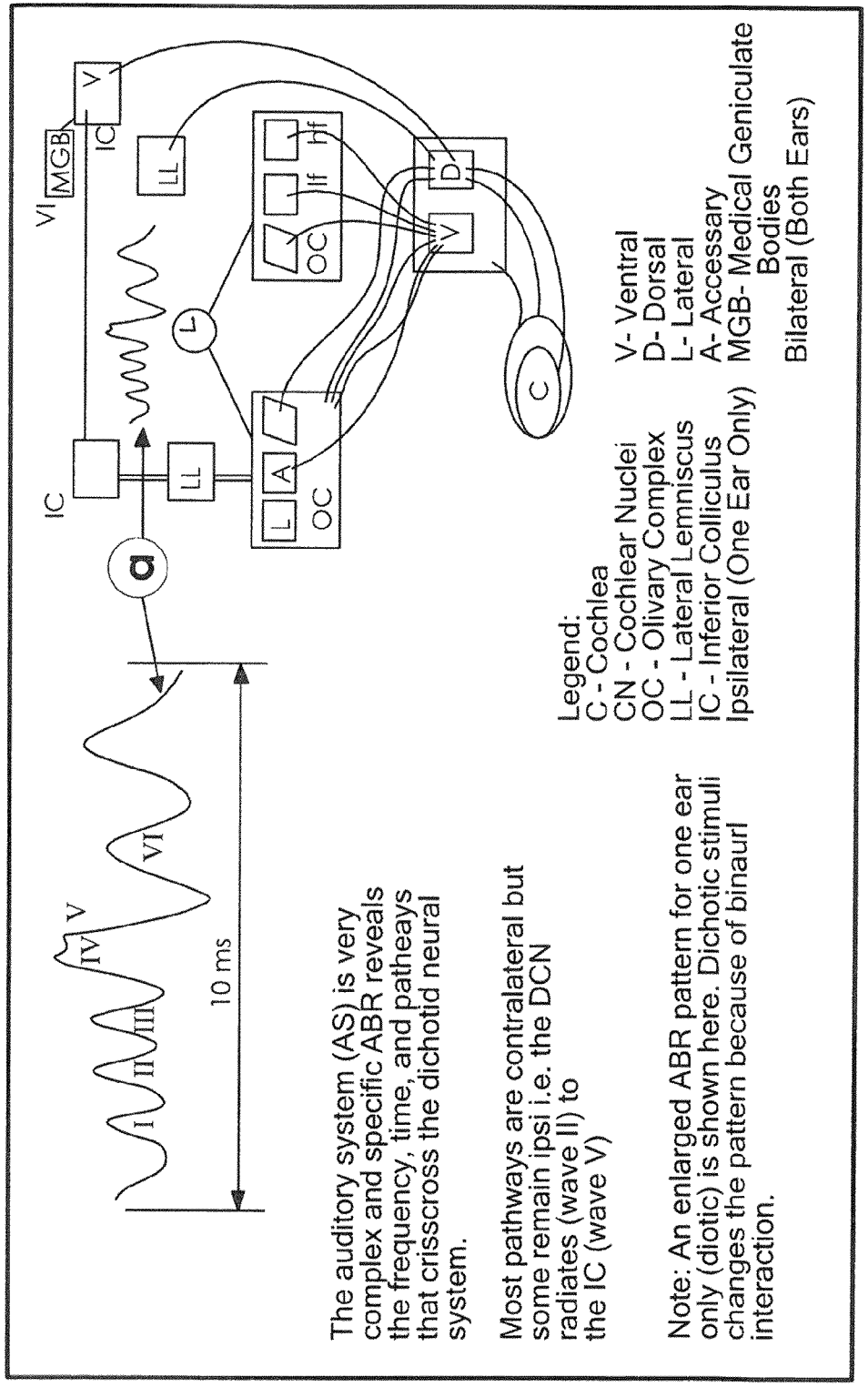
FIG. 1 is a schematic view, showing a prior art process.
Figure 2:
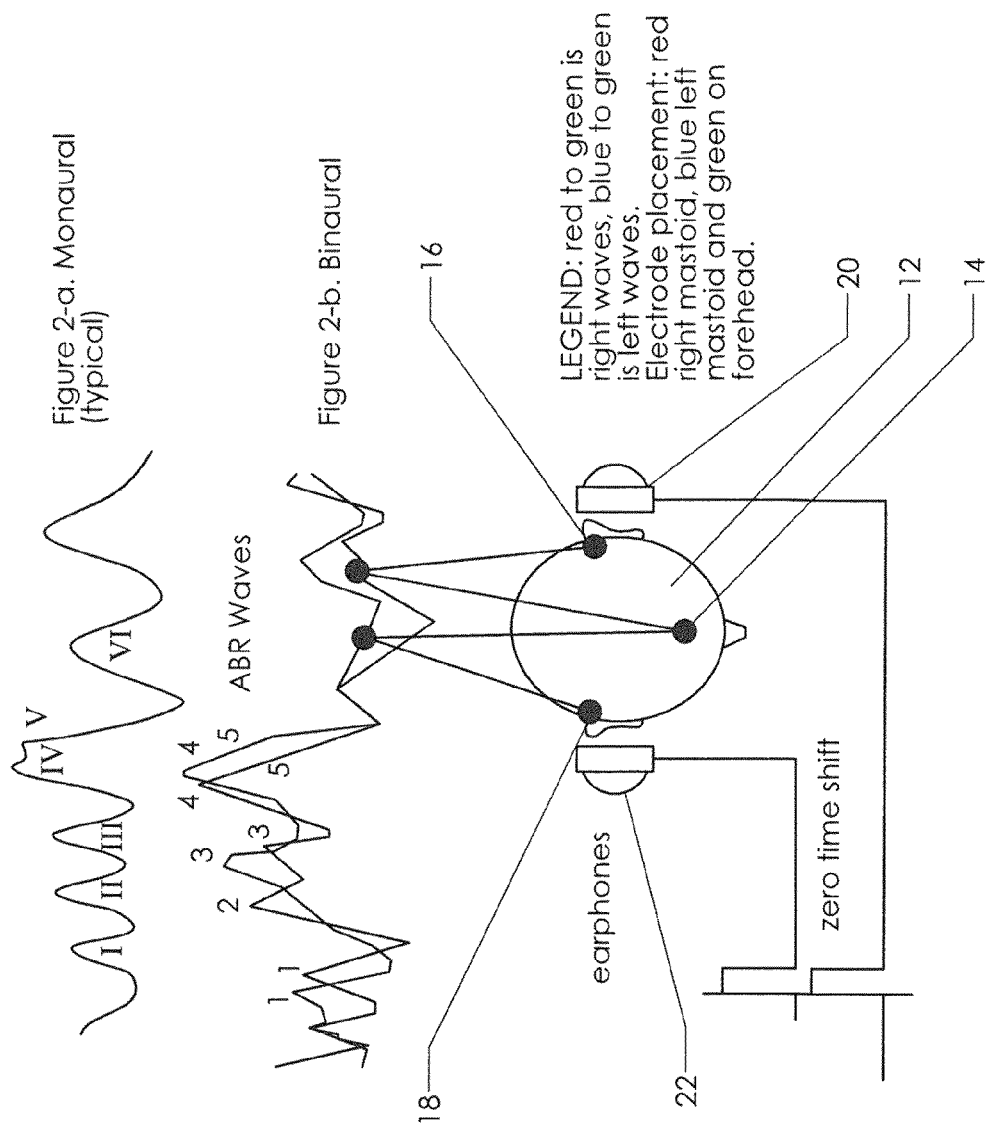
FIG. 2 is a schematic view, showing monaural and binaural waveforms.
Figure 3:
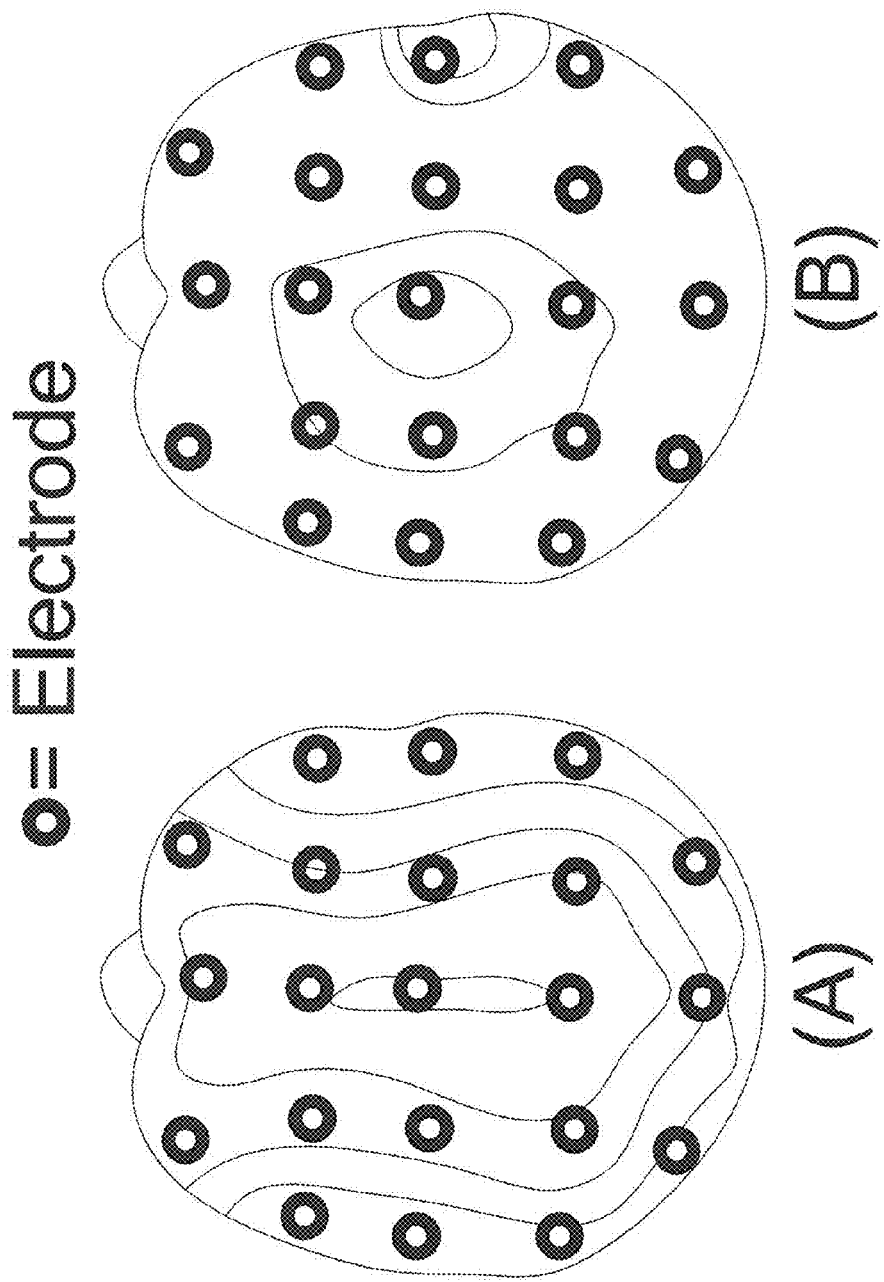
FIG. 3 is a schematic view, showing a multiple electrode array.
Figure 4:
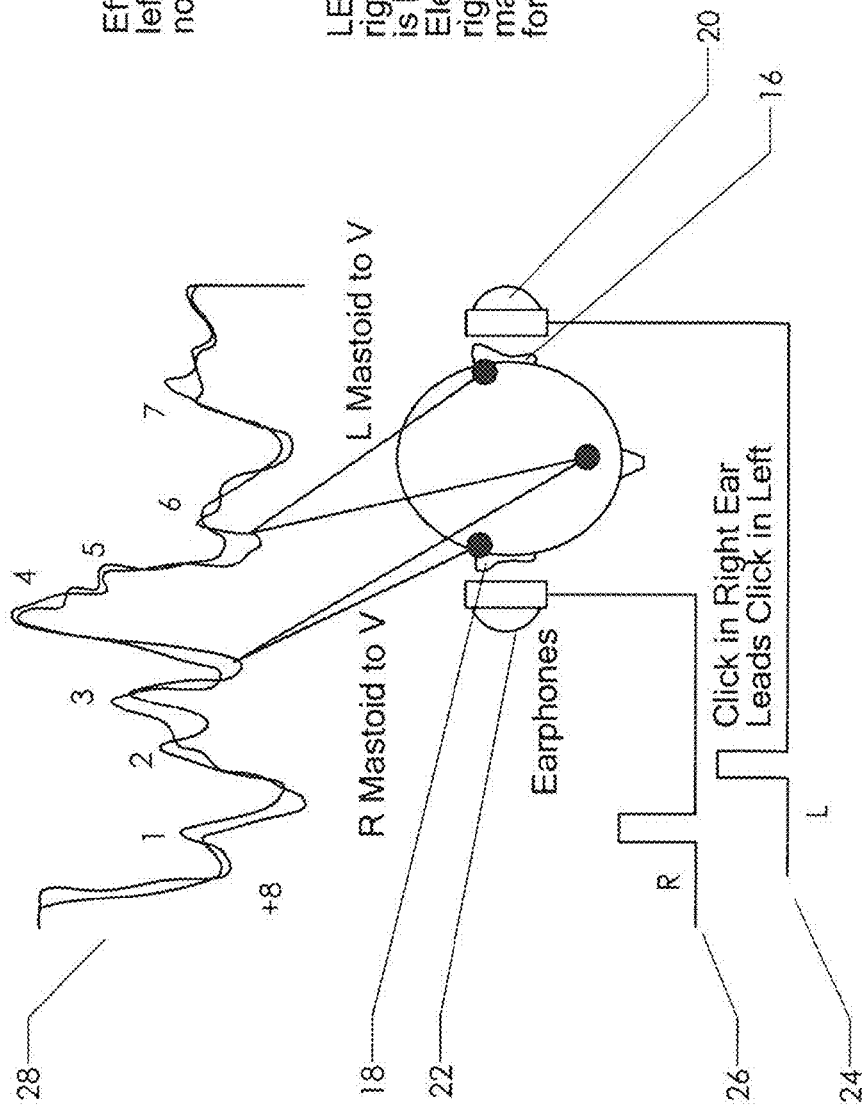
FIG. 4 is a schematic view, showing data from a right handed subject.
Figure 5:
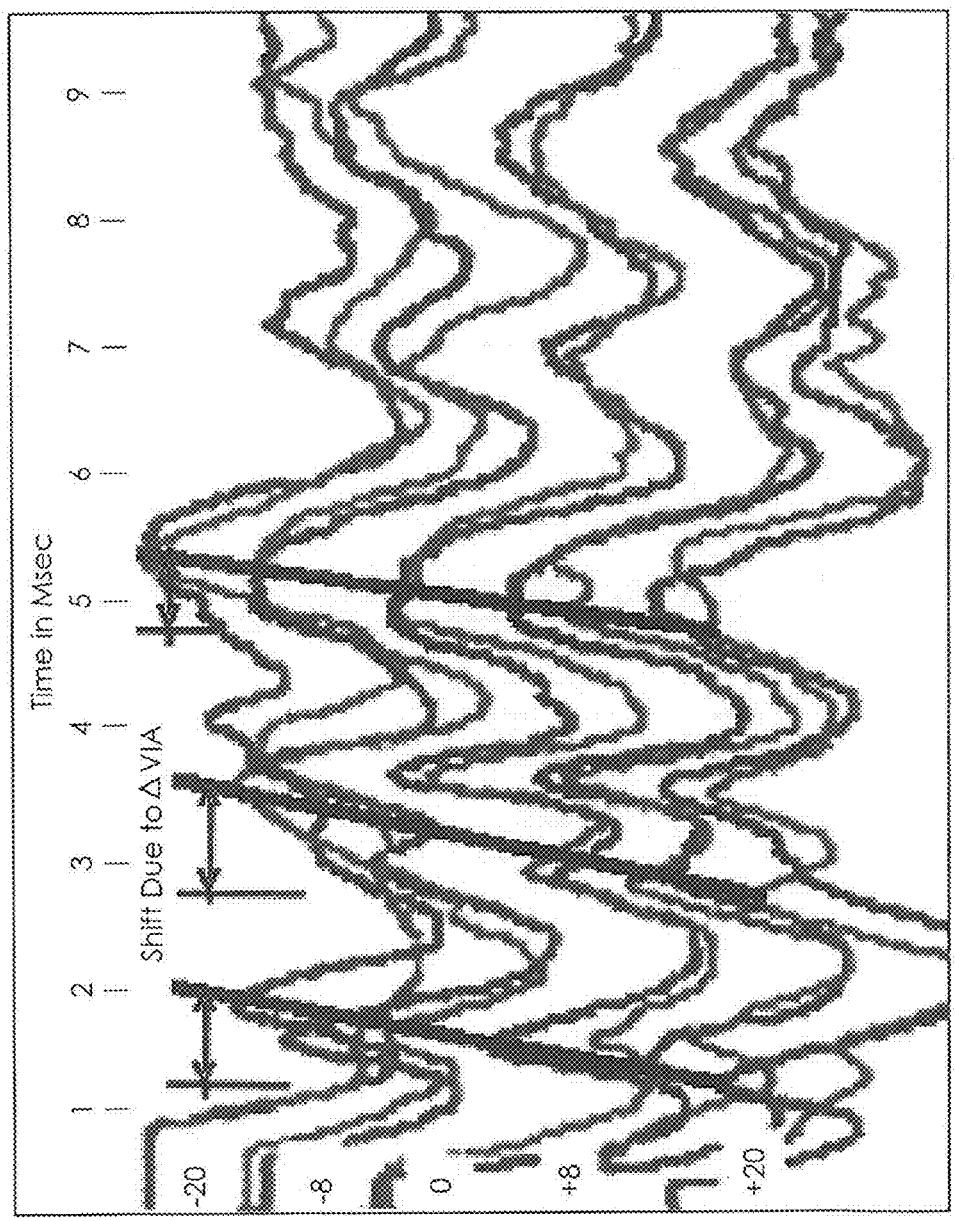
FIG. 5 is a schematic view, showing data charted on a graph.

| REFERENCE NUMERALS IN THE DRAWINGS | |
|---|---|
| 12 | head |
| 14 | ground electrode |
| 16 | left electrode |
| 18 | right electrode |
| 20 | left earphone |
| 22 | right earphone |
| 24 | left stimulus |
| 26 | right stimulus |
| 28 | ABR |
| 30 | left ear signal |
| 32 | right ear signal |
| 34 | left ear controls |
| 36 | right ear controls |

DETAILED DESCRIPTION

Phonemic VIA

A simple click is in the time domain for the auditory pathways (see FIG. 1) and can be tracked as it passes through the auditory neural stations. Phonemic stimuli, on the other hand, are in all of the critical detection areas of the binaural/dichotic analysis and are not as easily delineated as simple clicks. Therefore more complex stimuli have been developed using speech as the basic construct. With such neural interventions as cochlear implants (CI) coming of age, and bilateral implants becoming de rigueur, a new stimulus is needed that provides bilateral markers generated by the interaction of the two implants. These bilateral markers must be correlated to follow the neural pathways through the proper sequencing toward the central processing apparatus.

Of course, phonemic information would be the stimulus of choice in the analysis of central processing in the presence of a normal audiogram. Therefore the establishment of markers in top-down and bottom up evaluation necessitates more information than the VIA or MAID alone, or even ABR, can provide, but should not depart from existing VIA stimulus construction. However, the ideal stimulus should include a more complex composition such as found in speech.

New Construction of Top-Down CAPD Stimuli Using VIA Theory

The MAID envelope with only the removal of the puretone serves the same purpose as the VIA. This change generates a new stimulus where the actual click is reduced while leaving the carrier constant. Click thresholds thus become true rather than relative. Also, the MAID now becomes a duality that moves to the next step without having to introduce a new stimulus for dichotic central testing. When moving from cochlear/retrocochlear testing to central testing only the puretone carrier is removed so that the comparison integrity is constant and remains reliable in the differential diagnosis paradigm. The same intensity difference ($\Delta I$) is situated onto a constant ongoing baseline stimulus that forms the framework for all bottom-up and top-down procedures.

Figure 6:
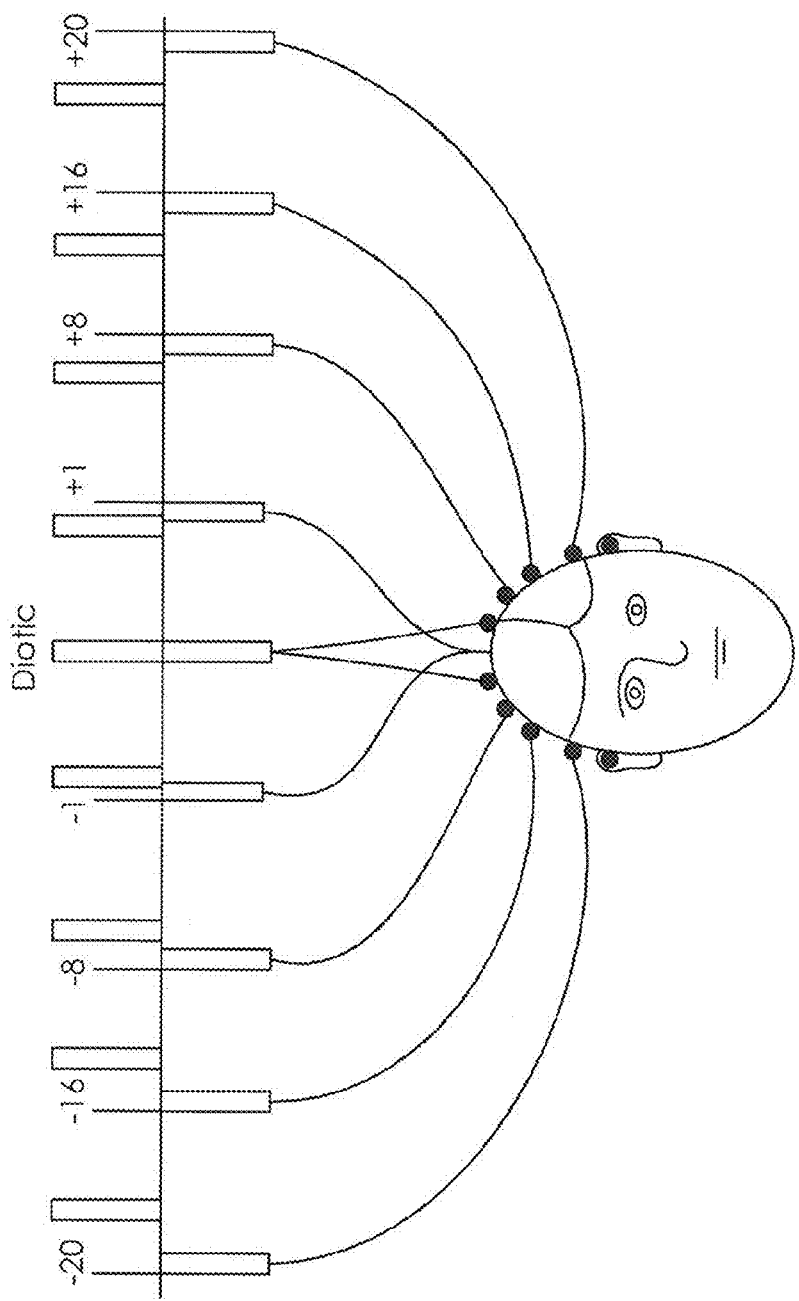
FIG. 6 is a schematic view, showing response delays in an individual.
Figure 8:
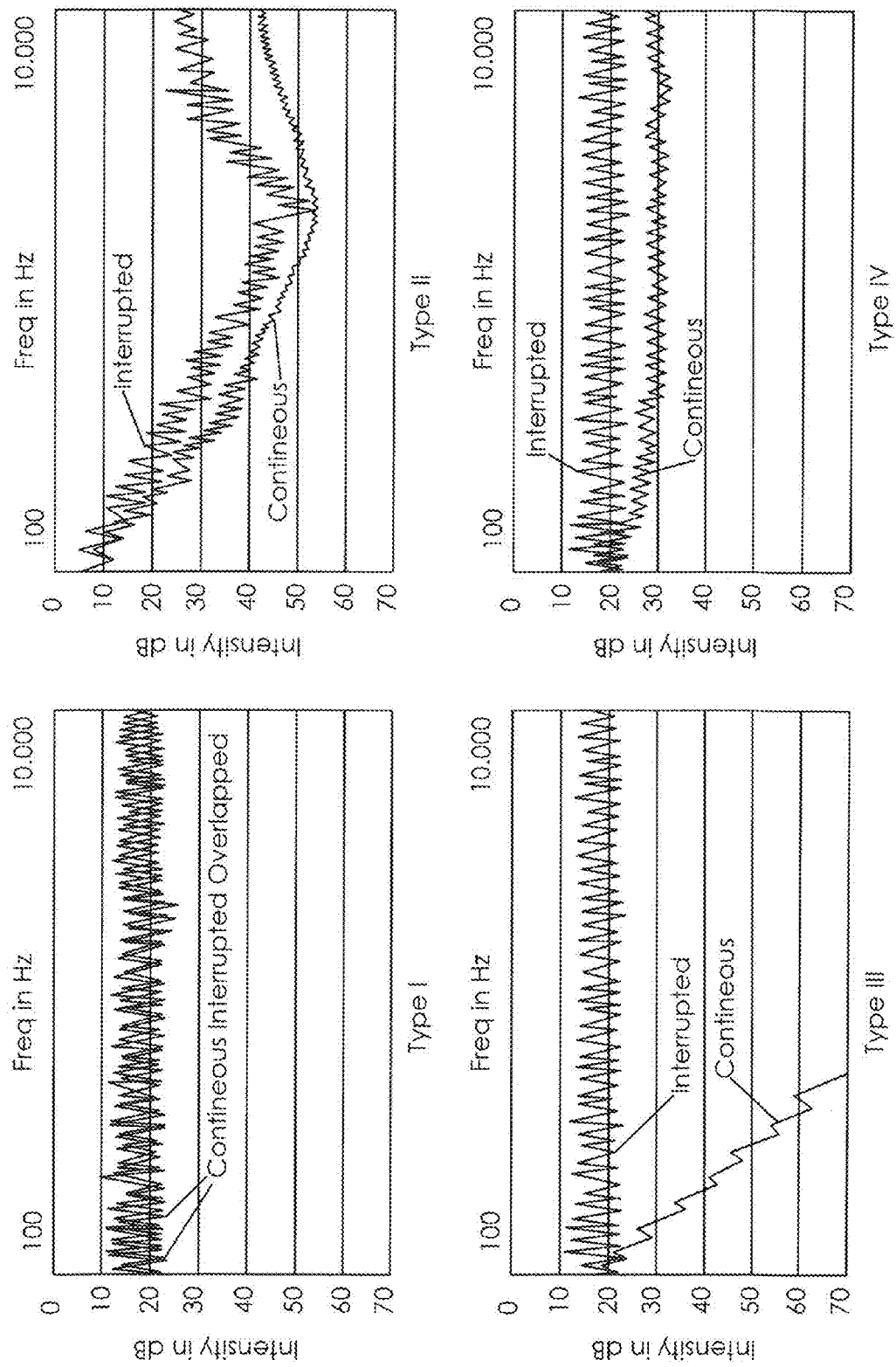
FIG. 8 is a schematic view, showing prior art Jerger Audiogram classes.
Figure 9:
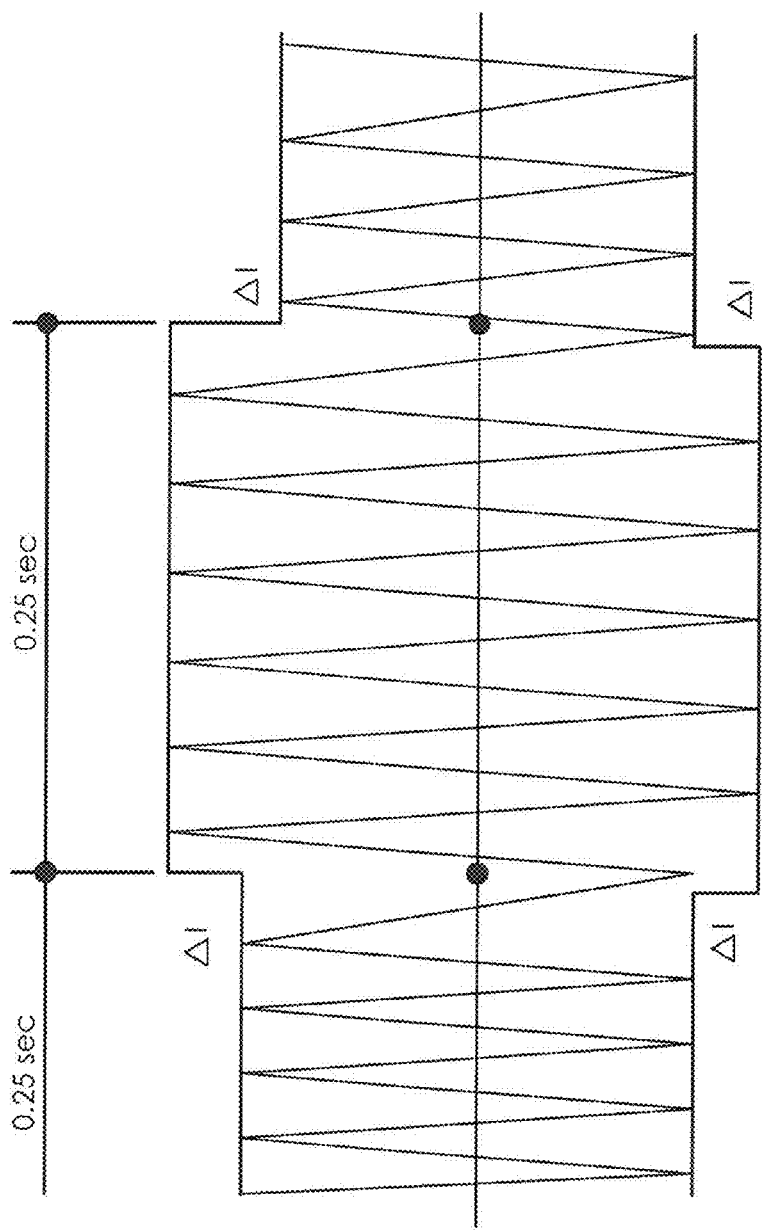
FIG. 9 is a schematic view, showing data from a prior art patent.
Figure 10:
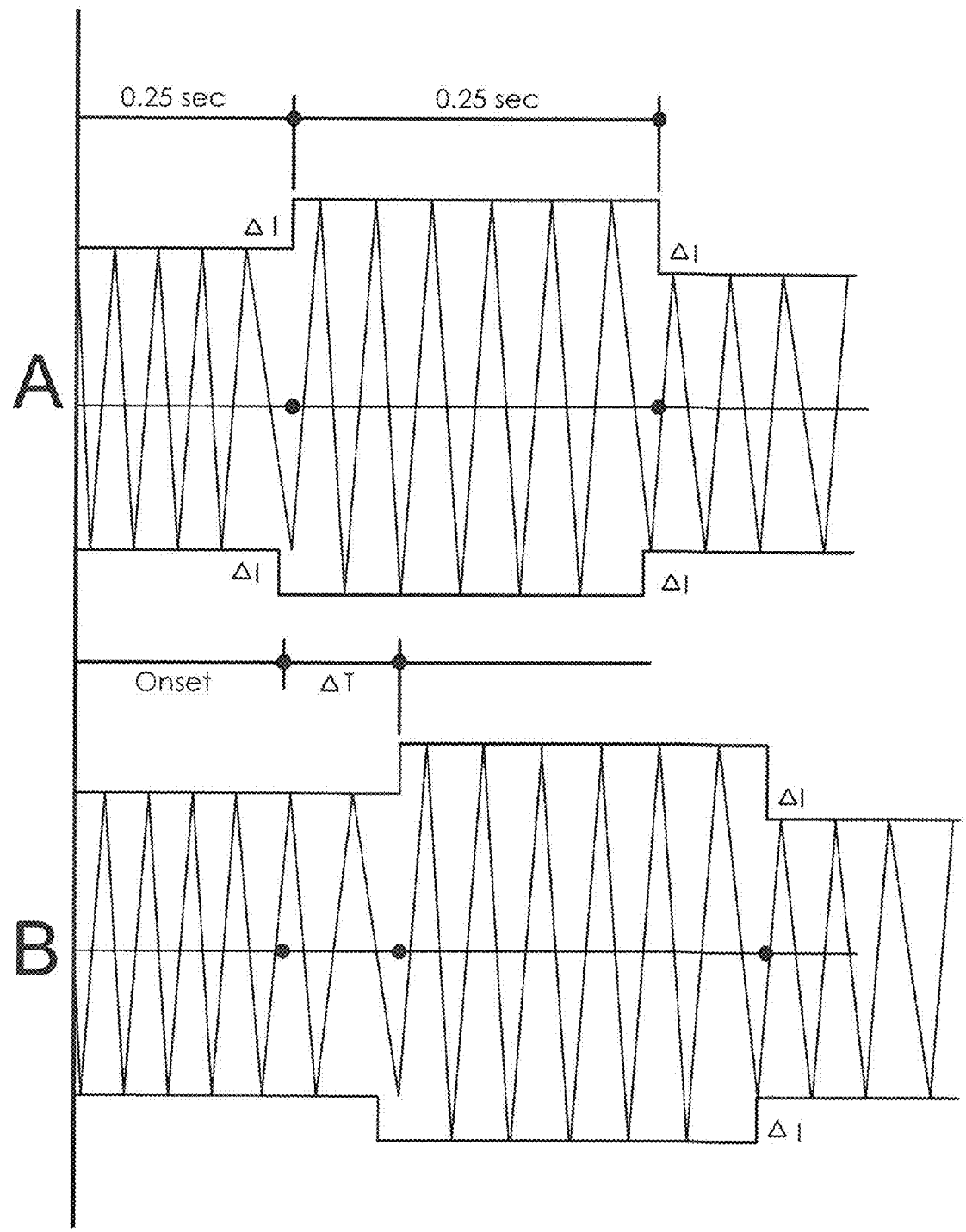
FIG. 10 is a schematic view, showing data charted on a graph in a dichotic test.
Figure 11:
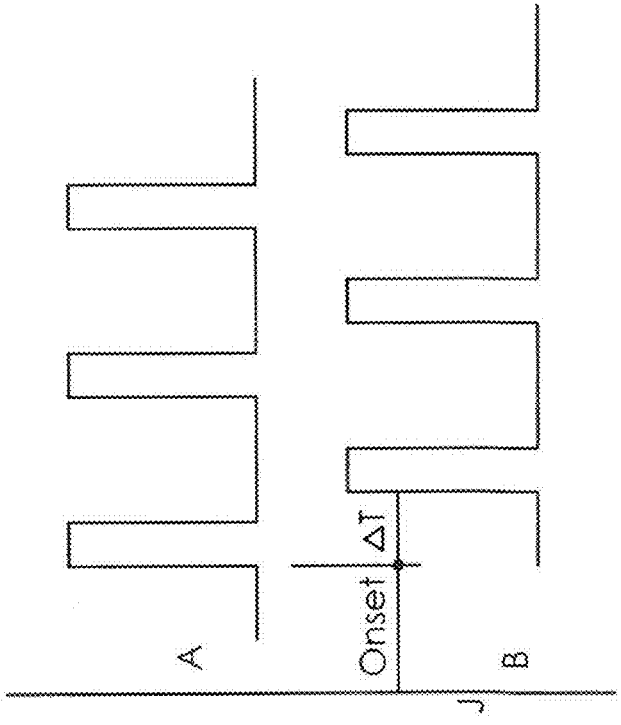
FIG. 11 is a schematic view, showing a MAID envelope.
Figure 12:
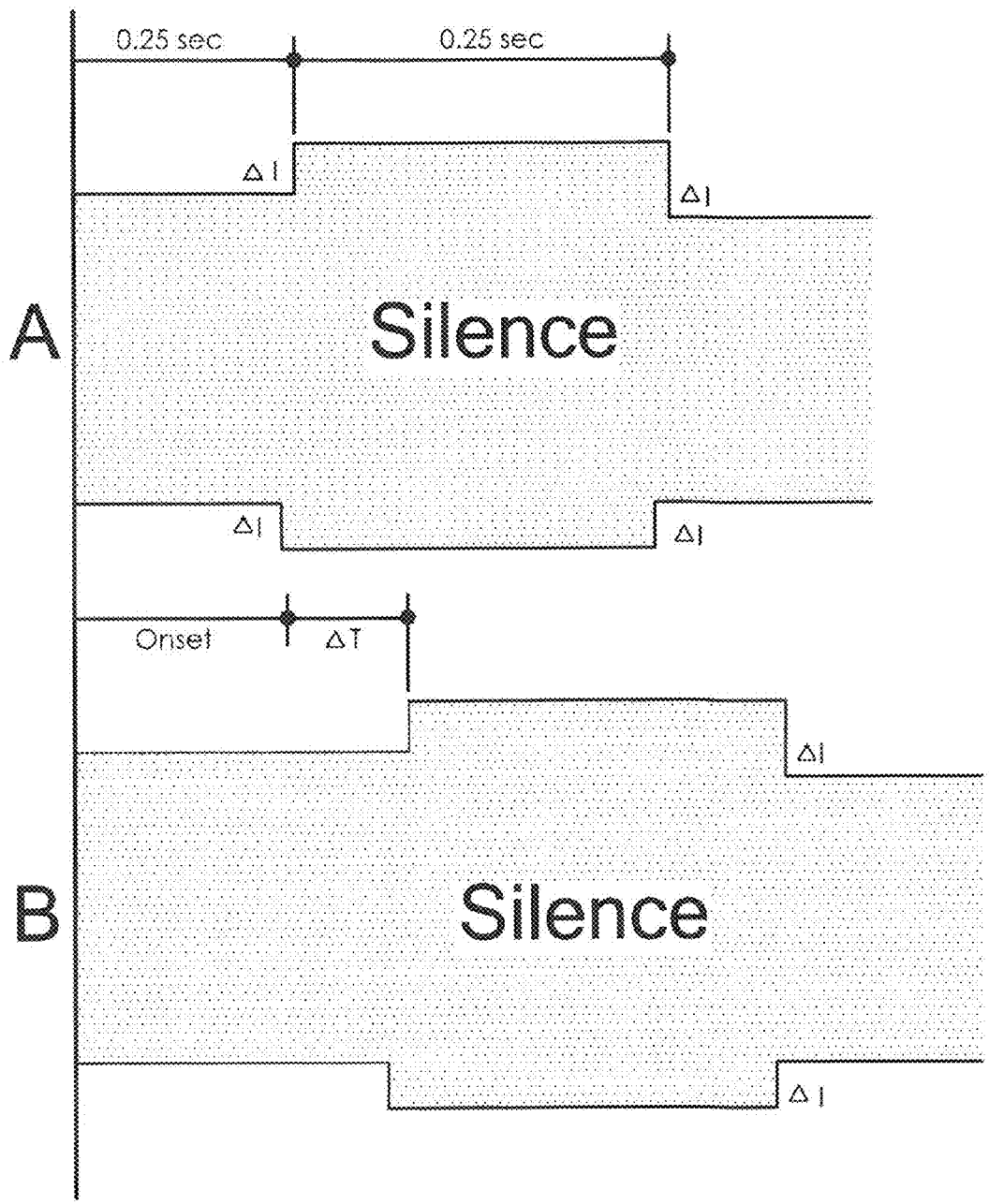
FIG. 12 is a schematic view, showing a Virtual Image Analysis (VIA) stimulus.
Figure 13:
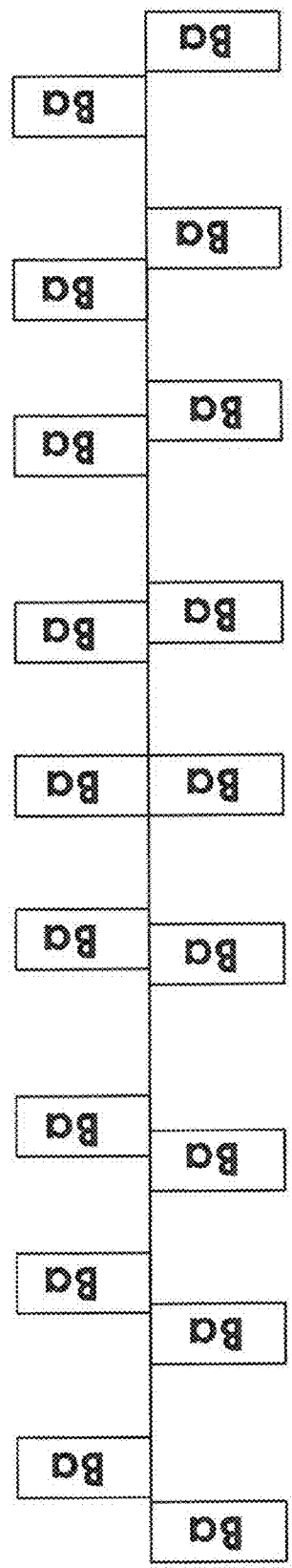
FIG. 13 is a schematic view of the process of phonemic virtual image analysis (pVIA).

This technique is applied in the basic phonemic paradigm. FIG. 13 shows the use of a single combination of phonemes in a dichotic array used in the pVIA (phonemic virtual image analysis) paradigm. The first level of phonemic stimulation is the use of a simple consonant/vowel unit ("Ba"). This stimulus replaces the click shown in FIGS. 6 and 11.

Figure 14:
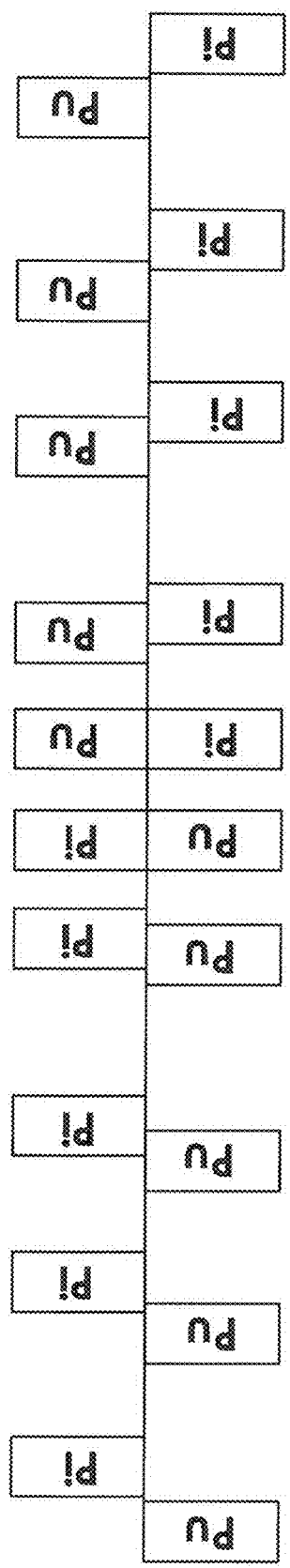
FIG. 14 is a schematic view of the pVIA paradigm with the syllables reversed.

In FIG. 14 the pVIA paradigm is again used but in this case the consonant/vowel unit results in a word. The syllables must be reversed for pVIA changes so that the user can perceive the same "word" throughout the test (The "word" need not have any actual meaning).

The pVIA paradigm must be flipped in the case to arrange the syllables to remain in the correct juxtaposition as a word and to reverse the lead/lag configuration. Here differing phonemic information is introduced to each ear requiring the central system to integrate the two parts into a word or phrase. The pVIA defines the optimum dichotic listening position for therapeutic use. It also provides the focal point for tinnitus cancellation processes.

The next step would be the use of event related potentials (ERP) and mismatched negativity (MMN) using the new stimulus.

In studies evaluating the proposed inventive methods, 33 subjects were selected from a group of ENT patients all complaining of head noises. The criteria for inclusion in the study were: (1) tonal tinnitus only, (2) moderate or better residual hearing, and (3) ability to carry out the required tasks.

ENT referral and routine audiological profiles were established on all subjects prior to the introduction of the tinnitus cancellation procedure. The audiological information was used only as a part of the subject selection process and to prevent over-stimulation of the first experimental trials.

Figure 15:
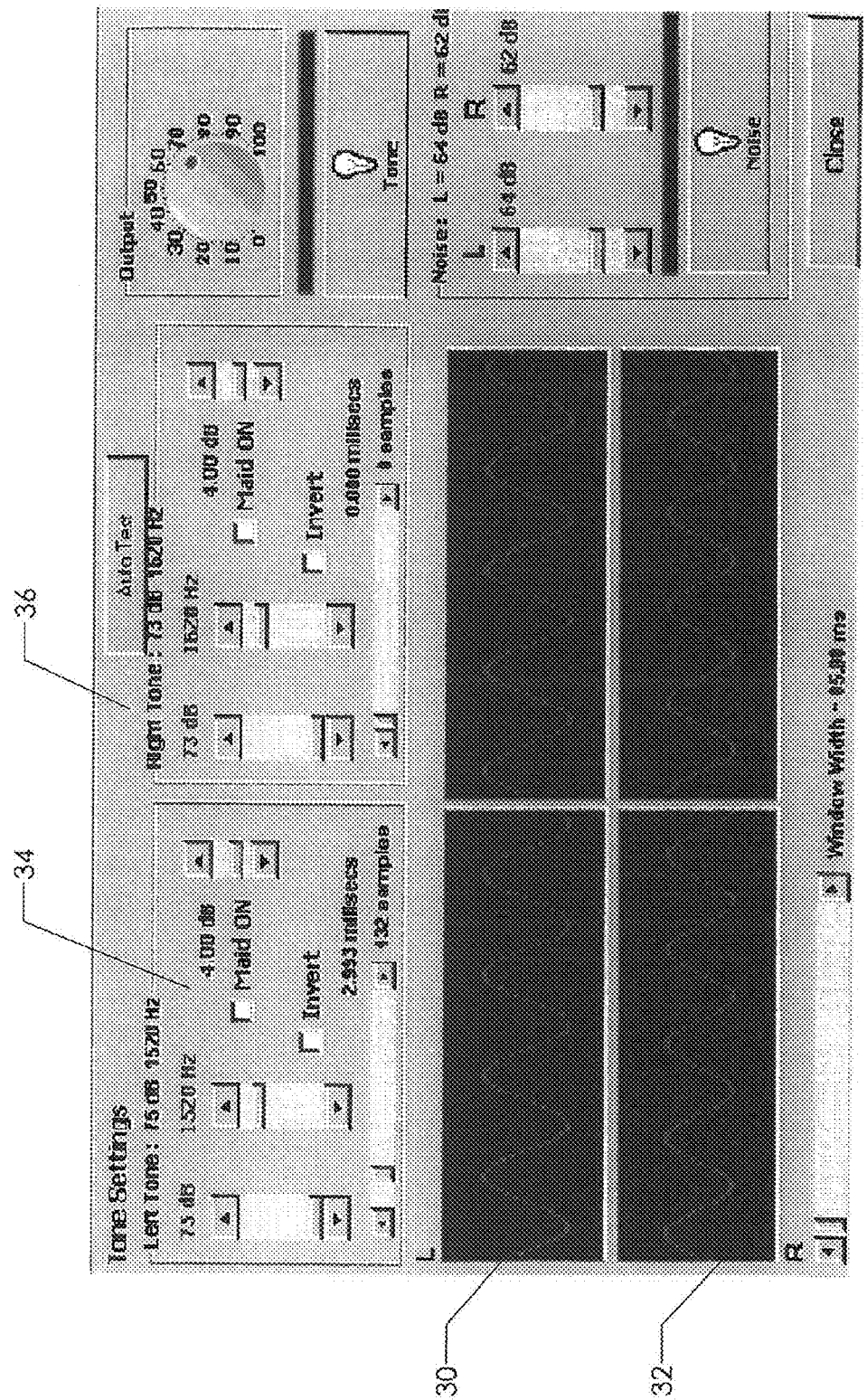
FIG. 15 is a screen shot view, showing prior art computer program with present data.

The experimental stimulus/response protocols, as well as the actual stimuli, were all in software under computer control. Stimuli were digitally generated and adjustable in 10 Hz-one dB steps. Screen shots of the computer display and stimulus/response choices are shown in FIG. 15. In this figure all of the stimulus options are shown. All parameters of the stimuli are visible in the four "traces" at the lower left of the screen. The reader should note that the phase of the right and left ears is shifted. The reader should also note that the MAID and VIA are employed as integral components of this apparatus.

In the particular embodiment illustrated, left ear controls 34 and right ear controls 36 are contained within a block of user-actuated options. Left ear signal 30 and right ear signal 32 are shown in the four graphical windows.

The sound transducers were Philmore 32 Ohm, Model 1035 extra-aural Digital Earphones with a frequency response of 20-20,000 Hz. Reference calibration was done electrically with a Sonido, Inc. PC Calibrator. The calibrator uses a digital comparator circuit that matches the electrical output of the computer sound card to that of an audiometer voltage applied across the transducers to produce a stimulus intensity of 67 dB SPL. This voltage is used to internally set the intensity controls of the computer for 1000 Hz.

The parameters to be measured (pitch, loudness, maskability, and residual inhibition) were selected, because of their traditional position in the psychoacoustics of tinnitus. The procedures were separated into four sections: (1) Thresholds; (2) Binaural Interaction; and (3) Training and Response Mode; and (4) Tinnitus reduction probes. Each of these three sections is detailed subsequently.

(1) Thresholds

Testing was begun at a frequency of 4000 Hz and a level of 40 dB SL per the pre-experimental audiogram. The intensity was raised or lowered in 1 dB steps to find the most comfortable diotic listening level. The tinnitus pitch match was found by a method of bracketing in 100 Hz steps and then fine-tuning in 10 Hz steps to the best pitch fit (BPF) (the frequency described by the patient as most accurately matching the perceived frequency of the tinnitus). If the BPF was reported to be noticeably different in the two ears a flip-flop ear-over-ear method of constant stimulus was used to establish a single BPF.

With the computer frequency set at the BPF the monaural absolute threshold (MAT) for intensity was then probed using the method of limits, a descending ascending series of down in one/up in one to the best loudness fit (BLF) (the loudness described by the patient as most accurately matching the perceived loudness of the tinnitus).

20 dB was then added to the MAT. Testing was then performed to establish the minimal auditory intensity differential (MAID) threshold at the BPF. This was done by descending in program-selected difference limens monaurally.

(2) Binaural Interaction

The virtual image analysis (VIA) measures binaural asymmetry. This technique was used to locate the position of equal binaural stimulation. It was previously found that binaural loudness at low signal-to-noise ratios changes with interaural phase differences. The VIA was generated by increasing the MAID to a ΔI of 6.0 bilaterally. The intensity presentation level was set at 10 db SL re the MAT of the BPF for each ear (equal loudness).

The phase of the left and right signals was then changed, lead or lag, in single sample steps (approximately 23 microseconds per step) by moving the two sinusoidal waveforms into a phase relationship where the subject reports the click to be in the perceived midplane (VIA zero or no perceived lead/lag between ears). During this procedure the ongoing puretone carrier will possibly decay (fade away) leaving only the derivative click. Abnormal tone decay is associated with central hearing dysfunction but partial decay in sensory hearing loss is not unusual.

(3) Training and Response Modes

The initial stimulus settings for training at the BPF were intensity @10 dBSL re MAT at the BPF; The MAID @, threshold plus 1 dB; and the VIA @ the perceived midplane (VIA perceived image of zero). The masking tone (MT) was then presented with the subject instructed to report the changes occurring over a 60 second trial period including 30 seconds of tone-on-tone masking (masking effect) and a 30 second residual inhibition period.

The test subject was seated in an armchair with an elbow placed on the arm of the chair with the elbow bent at 90 degrees to the arm of the chair. The subject was told to report verbally what he or she heard including the presence and relative magnitude of the tinnitus before the experimental trial was begun. Once it was clear that the subject understood the task, a trial was started by having the subject listen for the masking tone and to lower his or her hand downward towards the chair arm gradually with the decaying tone (NOT the decaying of the tinnitus itself). If the tone completely decayed the subject's hand would be resting on the chair arm at the end of the trial.

The subject was then instructed to lift his or her hand from the chair arm to 90 degrees if the tinnitus was unchanged from the pre-masking state or to raise his or her hand gradually at the rate of the returning tinnitus. Hence, the subject could "quantify" the amount of tone decay and the residual effects of the tone-on-tone masking by the range of the arm between 90 degrees and the hand resting on the chair arm (0 degrees). A final training step removed the MAID so as to not provide a clue as to when the masking tone was turned off. The training sessions were repeated as many times as necessary to assure the subject had an understanding of the task.

The intensity was then decreased in 2 dB steps to a level of 4 dB where cancellation probes were begun. The MAID (click) was presented during training trials as a reference for the subject to determine when the tone ended. This was turned off during the cancellation probes. Later studies showed that in some subjects leaving the MAID on contributed to the cancellation effect.

(4) Tinnitus Reduction Probes

The initial reduction probe was done with the intensity @4 dBSL re MAT at the BPF; the MAID (click) off; the VIA @ the perceived midplane (VIA perceived image of zero); and the subject responding by the hand signals.

The second reduction probe was done with all of the stimulus parameters set as in the initial reduction settings except the phase was shifted to fit the identified midline in degrees determined by sweeping the puretone VIA to a point of reduced tinnitus.

Figure 16:
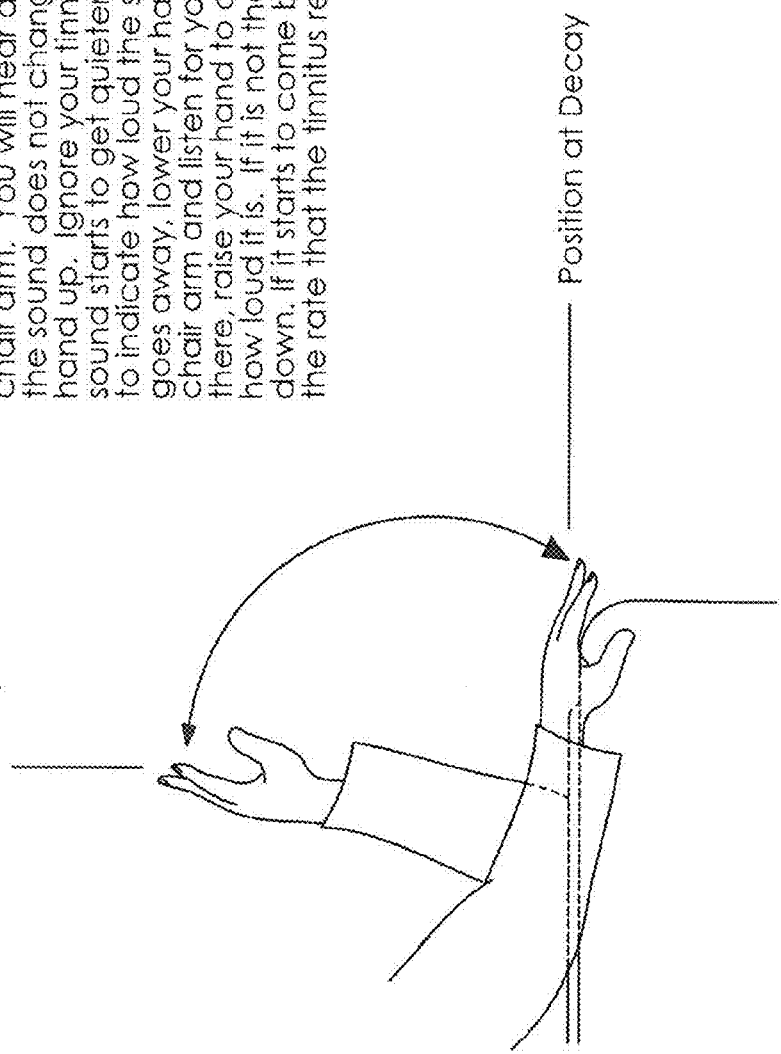
FIG. 16 is a perspective view, showing the present process.

The point defined in the second reduction probe was then used as the probe stimulus. Each subject was given a sketch similar to the one shown in FIG. 16 and given the instructions shown in the box. The perceived tone and tinnitus loudness was "quantified" by the angle of the responding subject's arm.

Figure 17:
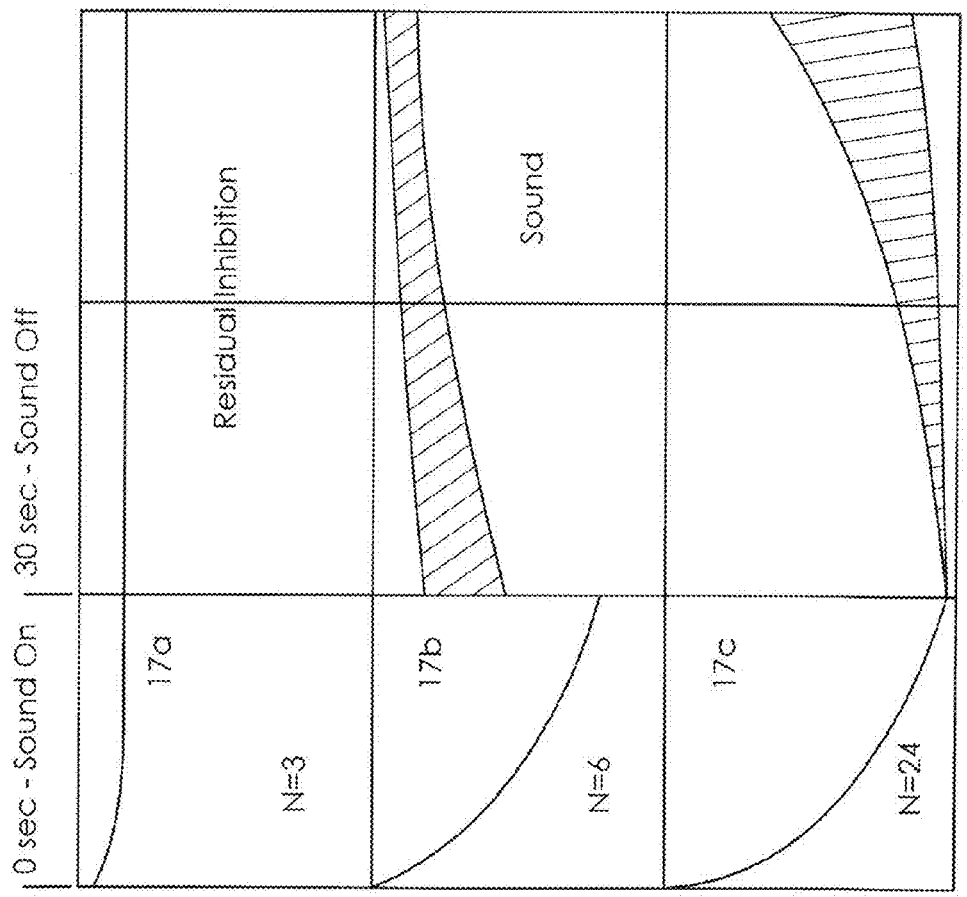
FIG. 17 is a schematic view, showing the present data.

The results are shown in FIG. 17. The subjects shown in FIG. 17a, lowered hand(s) no more than 75-80 degrees (indicating no NORMAL tone decay). The Subjects shown in FIG. 17b lowered hand(s) to no more than 15-30 degrees and quickly raised them to indicate presence of tinnitus. The shaded area on the right of FIG. 17b indicates the presence of, and the range of, residual inhibition. The Subjects shown in FIG. 17c lowered hand(s) all the way to the chair arm indicating total normal tone decay. The shaded area on the right of FIG. 17c indicates the "amount" of residual inhibition and the gradual return of tinnitus once the MAID was removed.

Of the 33 subjects only three (3) reported no tone decay or residual inhibition (FIG. 17a). Six (6) subjects reported tone decay with little or no residual inhibition at any setting (FIG. 17b). Six (6) subjects reported decay of both MAID and tinnitus with residual inhibition at no lead/lag (zero VIA) (FIG. 17c). Twelve (12) subjects reported decay of both tone and tinnitus with residual inhibition at left leads right (FIG. 17c) and six (6) subjects reported decay of both tone and tinnitus with residual inhibition at right leads left (FIG. 17c).

The standard clinical tone decay test uses a 1-minute sample at 5 dB. Because of the number of pre-experimental procedures and the number of experimental trials necessary for the present study the sample period was lowered to 30 seconds at 4 dB. This change in procedure could affect the number of subjects who did not experience normal tone decay in this study. However, in the application of these data in a tinnitus cancellation procedure, the tone-on time would not be set at an experimental time limit but would be left on for as long as necessary for the tone to decay and for the tinnitus tone-on-tone residual inhibition to occur and linger. This study demonstrated that near-threshold procedures are effective in reducing tinnitus. The study did not attempt to find the optimum condition(s) for each individual subject beyond the initial effective tone-on-tone masking and its phase relationship upon the subjective cancellation of tonal tinnitus.

In FIG. 17c there is a noted failure of the phase shift to cause residual inhibition of the tinnitus. The instructions were for the subject to lower his hand to the chair arm when the tone had gone away. However, tone decay is not an absolute and may appear to be complete when it is not. Therefore, when the tone is turned off the subject immediately realizes that it WAS still on and he or she reacts to that experience rather than focusing on the tinnitus condition. Extended MAID will probably terminate this effect.

Three subjects (FIG. 17a) reported no tone decay of any kind. Normal tone decay is an undeniable psychoacoustic event and should be present, to some degree, in every subject. The reason for their failure to experience normal tone decay will remain a topic for future exploration.

The preceding description contains significant detail regarding the novel aspects of the present invention. It should not be construed, however, as limiting the scope of the invention but rather as providing illustrations of the preferred embodiments of the invention. The scope of the invention should thus be set by the following claims rather than the examples given.

Having described my invention, I claim:

1. A method for reducing the perception of tinnitus in a human subject, comprising:
   a. providing a left ear phone directing left audible stimuli into a left ear of said human subject;
   b. providing a right ear phone directing right audible stimuli into a right ear of said human subject;
   c. providing an audible stimuli generator configured to generate said left and right audible stimuli;
   d. determining a best pitch fit for said tinnitus in said human subject;
   e. determining a midplane virtual image for said human subject by sweeping a phase of one of said left and right audible stimuli with respect to the other until said human subject reports perceiving said left and right audible stimuli as lying spatially on a midplane of said human subject;
   f. sweeping a phase of said one of said left and right audible stimuli with respect to the other until said human subject reports perceiving a point of reduced tinnitus;
   g. recording said values for best pitch fit and phase; and
   h. thereafter applying said values for best pitch fit and phase to said patient in order to reduce said perceived tinnitus.

* * * * *